United States Patent
Woodward et al.

(10) Patent No.: US 11,857,537 B2
(45) Date of Patent: *Jan. 2, 2024

(54) USE OF PROSTACYCLIN ANTAGONISTS FOR TREATING OCULAR SURFACE NOCICEPTION

(71) Applicant: JENIVISION INC., Irvine, CA (US)

(72) Inventors: David Frederick Woodward, Lake Forest, CA (US); Weizhen Wang, Irvine, CA (US)

(73) Assignee: JENIVISION INC., Irvine, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/210,213

(22) Filed: Mar. 23, 2021

(65) Prior Publication Data

US 2021/0212993 A1 Jul. 15, 2021

Related U.S. Application Data

(63) Continuation of application No. 16/562,063, filed on Sep. 5, 2019, now abandoned, which is a continuation (Continued)

(51) Int. Cl.
*A61K 31/4168* (2006.01)
*A61K 9/48* (2006.01)
(Continued)

(52) U.S. Cl.
CPC ........ *A61K 31/4168* (2013.01); *A61K 9/0048* (2013.01); *A61K 9/0051* (2013.01); *A61K 31/195* (2013.01); *A61K 31/21* (2013.01);
*A61K 31/343* (2013.01); *A61K 31/404* (2013.01); *A61K 31/421* (2013.01);
(Continued)

(58) Field of Classification Search
CPC .......................... A61K 31/4168; A61K 9/0048
See application file for complete search history.

(56) References Cited

U.S. PATENT DOCUMENTS

| | | | |
|---|---|---|---|
| 5,480,900 A | 1/1996 | Desantis, Jr. et al. | |
| 6,184,242 B1 * | 2/2001 | Bley | C07D 401/10 548/333.1 |

(Continued)

FOREIGN PATENT DOCUMENTS

| | | |
|---|---|---|
| CN | 1216762 A | 5/1999 |
| JP | H11140057 A | 5/1999 |
| WO | WO-2017132115 A1 | 8/2017 |

OTHER PUBLICATIONS

Johnstone "Keratoconjunctivitis sicca (dry eye)" https://www.tandfonline.com/doi/pdf/10.1080/20786204.2013.10874340 (Year: 2013).*

(Continued)

*Primary Examiner* — Shengjun Wang
(74) *Attorney, Agent, or Firm* — Wilson Sonsini Goodrich & Rosati

(57) ABSTRACT

The present invention relates generally to the use of compositions and methods for treating nociceptive events that occur on the ocular surface in association with dryness, injury, environmental pollutants, and infectious and non-infectious diseases. Specifically, the present invention is directed to the use of certain compounds for treating for treating ocular pain or ocular discomfort.

16 Claims, 2 Drawing Sheets

Related U.S. Application Data of application No. 15/710,438, filed on Sep. 20, 2017, now abandoned, which is a continuation of application No. 15/006,085, filed on Jan. 25, 2016, now Pat. No. 9,827,225.

(51) Int. Cl.

| | |
|---|---|
| A61K 31/505 | (2006.01) |
| A61K 31/404 | (2006.01) |
| A61K 31/195 | (2006.01) |
| A61K 31/421 | (2006.01) |
| A61K 31/4965 | (2006.01) |
| A61K 45/06 | (2006.01) |
| A61K 31/343 | (2006.01) |
| A61K 31/21 | (2006.01) |
| A61K 38/13 | (2006.01) |
| A61K 9/00 | (2006.01) |

(52) U.S. Cl.
CPC ........ *A61K 31/4965* (2013.01); *A61K 31/505* (2013.01); *A61K 38/13* (2013.01); *A61K 45/06* (2013.01)

(56) References Cited

U.S. PATENT DOCUMENTS

| | | | |
|---|---|---|---|
| 9,820,954 B2 | 11/2017 | Woodward et al. | |
| 9,827,225 B2 | 11/2017 | Woodward et al. | |
| 2002/0035264 A1* | 3/2002 | Kararli | A61K 47/10 |
| | | | 564/81 |
| 2013/0165665 A1 | 6/2013 | Kangasmetsa et al. | |
| 2014/0275238 A1 | 9/2014 | Wang et al. | |
| 2017/0209418 A1 | 7/2017 | Woodward et al. | |
| 2018/0008578 A1 | 1/2018 | Woodward et al. | |

OTHER PUBLICATIONS

Acosta et al., Comparative effects of the nonsteroidal anti-inflammatory drug nepafenac on corneal sensory nerve fibers responding to chemical irritation. Invest Ophthalmol Vis Sci 48(1):182-188, 2007.
Acosta et al., Sensations evoked by selective mechanical, chemical and thermal stimulation of the conjunctiva and cornea. Invest Ophthalmol Vis Sci 42(9):2063-2068, 2001.
Acosta MC et al., Changes in mechanical, chemical, and thermal sensitivity of the cornea after topical application of nonsteroidal anti-inflammatory drugs. Invest Ophthalmol Vis Sci 46:282-286, 2005.
Bates B et al., Prolonged analgesic response of cornea to topical resiniferatoxin, a potent TRPV1 agonist. Pain 149(3):522-528, 2010.
Belmonte C et al., Measurement of corneal sensitivity to mechanical and chemical stimulation with a CO2 esthesiometer. Invest Ophthalmol Vis Sci 40(2):513-519, 1999.
Belmonte C et al., What causes eye pain? Curr Ophthalmol Rep 3:111-121, 2015.
Bielory et al. Efficacy and Tolerability of Newer Antihistamines in the Treatment of Allergic Conjunctivitis. Drugs 65(2):215-228 (2005).
Bley KR et al., RO1138452 and RO3244794: characterization of structurally distinct, potent and selective IP (prostacyclin) receptor antagonists. Br J Pharmacol 147:335-345 (2006).
Brittain RT et al., AH23848: a thromboxane receptor-blocking drug that can clarify the pathophysiologic role of thromboxane A2. Circulation 72(6):1208-1218, 1985.
Calleja et al., Acid-sensing ion channels detect moderate acidifications to induce ocular pain. Pain 156(3):483-495, 2015.
Chang et al., Management of psoriatic arthritis from the view of the dermatologist. Nature Rev Rheumatol 7:588-598, 2011.
Chen X et al., Reduction by antiinflammatory drugs of the response of corneal sensory nerve fibers to chemical irritation. Invest. Ophthalmol Vis Sci, 38:1944-1953, 1997.
Cheng-Bennet et al. Lack of prostaglanfin F2alpha metabolism by human ocular tissues. Invest Ophthalmol Vis Sci 31(7):1389-1393, 1990.
Cho MJ and Allen MA, Chemical Stability of Prostacyclin (PGI2) in aqueous solutions. Prostaglandins 15(6):943-954, 1978. (Best available copy).
Coppens et al., Treatment of postoperative pain after ophthalmic surgery. Bull Soc Beige Ophthalmol 285:27-32, 2002.
Doi Y et al., Central nociceptive role of prostacyclin (IP) receptor induced by peripheral inflammation. NeuroReport 13:93-96, 2002.
European Patent Application No. 17744748.9 Extended European Search Report dated Jan. 14, 2020.
Gao et al., A 7-day oral treatment of patients with active rheumatoid arthritis using the prostacyclin analog iloprost: cytokine modulation, safety, and clinical effects. Rheumatol Int 22:45-51, 2002.
Gatta L et al., Discovery of prostamide F2alpha and its role in inflammatory pain and dorsal horn nociceptive neuron hyperexcitability. Plos One 7:e311111, 12 pages, 2012.
Gonzalez et al., Reduction of capsaicin-induced ocular pain and neurogenic inflammation by calcium antagonists. Invest Ophthalmol Vis Sci 34:3329-3335, 1993.
Goyal et al.: Blockade of Prolymphangiogenic Vascular Endothelial Growth Factor C in Dry Eye Disease. Arch Ophthalmol. 130(1):84-89 (2012).
Hessen et al. Dry Eye: an Inflammatory Ocular Disease. J Ophthalmic Vis Res 9(2):240-250 (2014).
Huang X et al., Amylin suppresses acetic-induced visceral pain and spinal c-fos expression in the mouse. Neurosci 165:1429, 17 pages, 2010.
Japanese Patent Application No. 2018-536488 Office Action dated Feb. 25, 2020.
Kanda H, et al., COX-1-dependent prostaglandin D2 in microglia contributes to neuropathic pain DP2 receptor in spinal neurons. Glia 61(6):943-956, 2013.
Kawakami, et al., Roles of thromboxane A2 and leukotriene B4 in radicular pain induced bu herniated nucleus pulposus. Journal of Orthopaedic Research, 19:472-477, 2001.
Kunori S et al., Involvement of prostaglandin F2alpha receptor in ATP-induced mechanical allodynia. Neurosci 163:362-371, 2009.
Lang et al., Formaldehyde and chemosensory irritation in humans: A controlled human exposure study. Regul Toxicol Pharmacal 50:23-36, 2009.
Loeser and Treede, The Kyoto protocol of IASP basic pain therapy. Pain 137:473-477, 2008.
Mayerhoefer et al.: Short-term outcome of painful bone marrow oedema of the knee following oral treatment with iloprost or tramadol: results of an exploratory phase II study of 41 patients. Rheumatology. 46:1460-1465 (2007).
Mexican Patent Application No. MX/a/2018/009125 Office Action dated Feb. 13, 2020.
Murata T et al., Altered pain perception and infammatory response in mice lacking prostacyclin receptor. Nature 388:678-682, 1997.
Murata Y et al., Peripheral and central distribution of TRPV1, substance P and CGRP of rat corneal neurons. Brain Res 1085:87-94, 2006.
Nakae et al., Functional role of prostacyclin receptor in rat dorsal root ganglion neurons. Neurosci Lett 388:132-137, 2005.
Oh-ishi S et al., Evidence for involvement of prostaglandin I2 as a major nociceptive mediator in acetic acid-induced writhing reaction: A study using IP-receptor disrupted mice. Eicosanoids and Other Bioactive Lipids in Cancer, Inflammation, and Radiation Injury. Kluwer Academic, Plenum Publishers, NY, Chapter 39, p. 265-268 , 1999.
Parra A., et al. Tear fluid hyperosmolality increases nerve impulse activity of cold thermoreceptor endings of the cornea. Pain 155:1481-1491, 2014.
PCT/US2017/014677 International Search Report and Written Opinion dated Jun. 12, 2017.

(56) References Cited

OTHER PUBLICATIONS

Pulichino et al., Prostacyclin antagonism reduces pain and inflammation in rodent models of hyperalgesia and chronic arthritis. J Pharmacal Exp Ther 319:1043-1050, 2006.
Rodrigues et al.: Topical Drug Delivery to the Posterior Segment of the Eye: Addressing the Challenge of Preclinical to Clinical Translation. Phar Res 35:245 5 pages (2018).
Schuh et al., Prostacyclin regulates spinal nociceptive processing through cyclic adenosine monophosphate-induced translocation of glutamate receptors. Anesthesiology 120:447-458, 2014.
Ueno A et al., Major roles of prostanoid receptors IP and EP3 in endotoxin-induced enhancement of pain perception. Biochem Pharmacal 62:157-160, 2001.
Urquhart et al., Identification of prostamides, fatty acyl ethanolamines, and their biosynthetic precursors in rabbit cornes. J Lipid Res 56:1419-1433, 2015.
U.S. Appl. No. 16/562,063 Office Action dated Aug. 14, 2020.
U.S. Appl. No. 16/562,063 Office Action dated Feb. 24, 2021.
U.S. Appl. No. 15/006,085 Office Action dated Jan. 26, 2017.
U.S. Appl. No. 15/006,085 Office Action dated Jul. 22, 2016.
U.S. Appl. No. 15/710,438 Office Action dated Nov. 15, 2018.
Vierboom et al., The significance of non-human primates as preclinical models of human arthritic disease. Exp Opinion on Drug Discovery 3:299-310, 2008.
Voilley N et al., Nonsteroid anti-inflammatory drugs inhibit both the activity and the inflammation-induced expression of acid-sensing ion channels in nociceptors. J Neurosci 21:8026-8033, 2001.
Wang et al. A Prostacyclin Analog, Cicaprost, Exhibits Potent Anti-Inflammatory Activity in Human Primary Immune Cells and a Uveitis Model. J Ocul Pharmacol Ther 33(3):186-192 (2017).
Wang JW et al., Multitargeting of selected prostanoid receptors provides agents with enhanced anti-inflammatory activity in marcophages. FASEB J, 30:394-404, 2016.
Wemmie et al., Acid-sensing ion channels in pain and disease. Nature Rev Neurosci 14(7):461-471, 2013.
Woodward et al. Characterization of a Model of Ocular Pain/ discomfort With Respect to Cyclo-oxygenase and Prostanoid Receptor Involvement. ARVO Annual Meeting Abstract. Investigative Ophthalmology & Visual Science 53:1803 (Mar. 2012).
Woodward et al., International union of basic and clinical pharmacology. LXXXIII: Classification of prostanoid receptors, updating 15 years of progress. Pharmacal Rev 63:471-538, 2011.

* cited by examiner

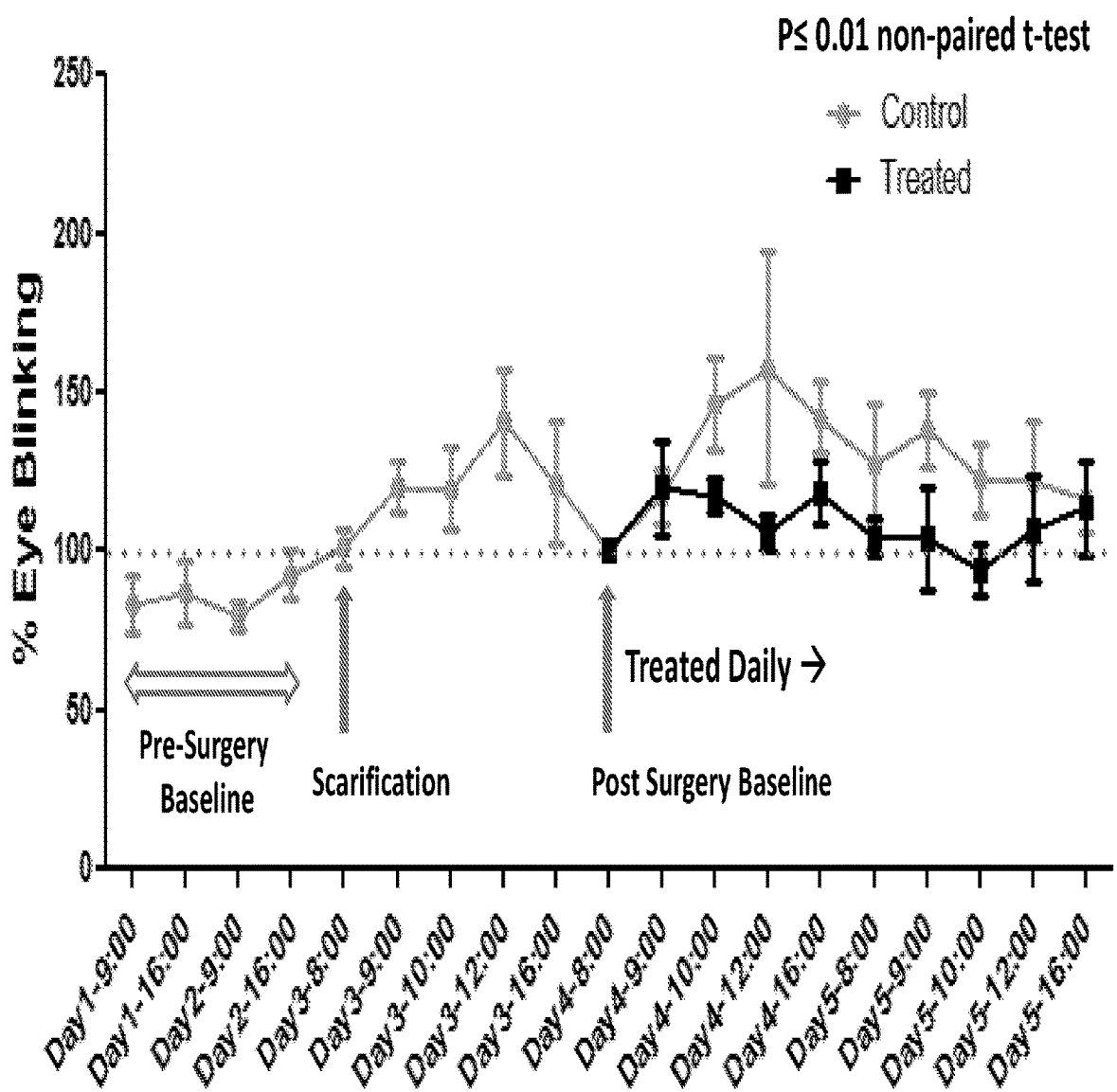
FIG. 1 Surgical Induced Eye Pain/Discomfort on Cynomolgus Monkey Eyes (n=4)

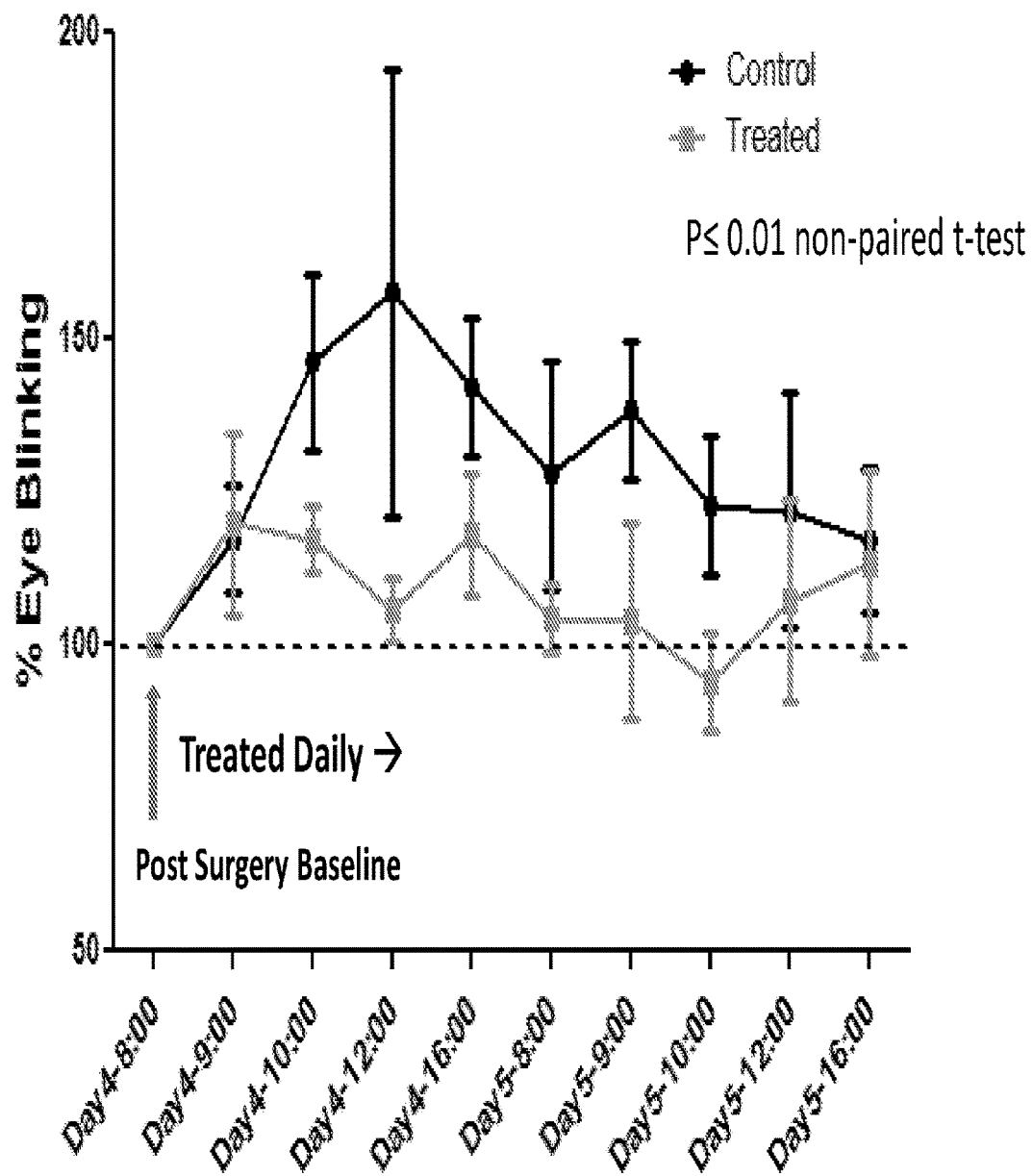
Fig. 2 Surgical Induced Eye Pain/Discomfort on Cynomolgus Monkey Eyes (n=4)

USE OF PROSTACYCLIN ANTAGONISTS FOR TREATING OCULAR SURFACE NOCICEPTION

CROSS-REFERENCE

This application is a continuation of U.S. application Ser. No. 16/562,063, filed Sep. 5, 2019, which is a continuation of U.S. application Ser. No. 15/710,438 filed Sep. 20, 2017, now abandoned, which is a continuation of U.S. application Ser. No. 15/006,085 filed Jan. 25, 2016, now issued as U.S. Pat. No. 9,827,225 on Nov. 28, 2017.

FIELD OF INVENTION

The present invention relates generally to the use of compositions and methods for treating the nociceptive events that occur on the ocular surface in association with dryness, injury, environmental pollutants, and infectious and non-infectious diseases. Specifically, the present invention is directed to the use of certain compounds for treating for treating ocular pain.

BACKGROUND OF THE INVENTION

The nociceptive events that may occur locally on the ocular surface are quite unique to the eye and, in the majority of cases, are best described as ocular surface irritation and discomfort. Symptoms unique to the eye include foreign body sensation, photosensitivity, photophobia and an actual sensation of dryness of the eye. Foreign body sensation is essentially identical to a "something in the eye" feeling, which may occur in varying degrees from discomforting but tolerable to intolerable in extreme cases. These foreign body sensations and other mild nociceptive events also promote a more rapid rate of blinking (nictation) and possibly tearing. This may be accompanied by a mild stinging or burning sensation. Photophobia and photosensitivity are unique to the eye and this hypersensitivity to light results in squinting and eye closure to relieve this unpleasant sensation.

Treatment of ocular pain and discomfort induced by dry-eye disease is an unmet medical need. For relief of post-surgical pain, the current standards of care are: (1) topical steroids, but long term use is associated with severe side effects; (2) NSAIDs, these have some effects only on surgical pain and are useful as pretreatments but are much less effective in reversing ongoing conditions. This is because NSAIDs only block the new synthesis of all prostanoids, leaving pre-existing ocular prostanoids in ongoing medical conditions to still interact with their receptors to cause pain and irritation. On the other hand, IP antagonist could treat ocular pain by blocking IP receptor, bypassing the need to attenuate prostanoid synthesis.

Artificial ocular surface wetting agents and lubricants provide some relief for ocular discomfort. The afflicted person may eventually present at the physician's office for treatment. There is no proven therapeutic intervention available to attenuate the nociceptive stimulation and neurotransmission at the ocular surface and resultant discomfort sensations.

The therapeutic modality that provided relief from ocular discomfort described herein is a prostacyclin (IP) receptor antagonist. In a model where ocular surface discomfort produced by mild corneal abrasion was reflected as an increased nictation rate, post-treatment with a prostanoid IP receptor antagonist essentially produced significant relief from ocular surface discomfort and reduced the nictation rate. It is also considered that a prostanoid IP receptor antagonist may be combined with ocular surface lubricants to provide further relief from ocular surface discomfort.

Nociceptors are situated on nerve endings and are the first element in communicating diverse chemical, thermal, and mechanical stimuli to the CNS (spinal cord and brain). Nociceptors roles differ greatly, with functions ranging from sensing blood pressure and $CO_2$ changes to mediating pain. The dull aching or sharp pain associated with injury, inflammation, infection and cancer is divided into two types. These are somatic pain arising from internal tissues and visceral pain arising from internal organs. In internal organs and tissues, the neuronal elements involved in initiating pain responses are polymodal nociceptors, which respond to local neurotransmitters. The initial neurotransmission is then relayed by nerves for central processing and translation into a perceived sensation. Peripheral nociception is yet a further category. Entirely different and unique sensations occur in peripheral nociception, which is confined to those surfaces exposed to the environment; ocular surface and skin and orifices (nasal and anal). These unique sensations include itch and perception of cold and hot.

In the domain of peripheral nociception, there is further divergence and differentiation. The nociceptive stimulation-response repertoire in the cornea possesses unique attributes. The neuronal responsive elements, the pharmacology of corneal nociception, and the quality and gradation of the perceived sensations following corneal insult or injurious stimuli, are unique. Nociceptive events associated with the cornea/ocular surface are those that elicit a sensation that may be discomforting, irritating, but painful only in the more extreme cases. Such responses essentially follow a graduation from discomforting/irritating and tolerable to painful and intolerable. Stimulation of corneal nociceptors (mechanoreceptors, chemoreceptors, thermoreceptors) elicit sensations that would not occur in other tissues. Provided below is an abbreviated compendium of the unique spectrum of events associated with corneal nociception.

1. Unique sensations experienced as a result of corneal nociception: photosensitivity, photophobia, dryness, foreign body sensation and tearing.
2. Corneal sensory nerve endings subserving unique sensations in the cornea:
   (a) Chemoreceptors; corneal receptors that mediate discomfort and irritation caused by environmental pollutants (Belmonte et al., 1999; Lang et al., 2008; Callejo et al., 2015);
   (b) Mechanoreceptors; corneal receptors that mediate a pricking sensation (Belmonte et al., 2015);
   (c) Thermoreceptors (cold): corneal receptors that mediate feeling of dryness (Parra et al., 2014), cooling, irritation (Belmonte et al., 1999); and,
   (d) Polymodal nociceptors; Mediate sensory responses from all irritant/noxious stimuli and mediate hyperalgesia and pain (burning, stinging) (Belmonte et al., 2015).
3. Receptor pharmacology of corneal surface nociception: Piezo 2 receptors mediate responses to mechanical forces; TRPV1/TPRPA1 receptors mediates responses to heat and chemical stimuli; TRPM8 receptors mediate the response to cold; ASIC receptors mediate the response to acids (Callejo et al., 2015; Belmonte et al., 2015). Non-steroidal anti-inflammatory agents are exert corneal analgesia by inhibiting nociceptors (Chen et al., 1997; Acosta et al., 2007).

Corneal nociception is unique on all levels. For this reason, in a litany of somatic and visceral pain conditions cited in various patents, corneal nociception is not mentioned and peripheral nociception is virtually ignored (U.S. Pat. Nos. 6,184,242; 6,596,876; 6,693,200; and 7,141,584, which are hereby incorporated by reference). This is likely because of the potential involvement of mechano- and chemo-nociceptors, in addition to polymodal nociceptors, in peripheral nociception. Nasal and anal nociception are ignored and cutaneous nociception is only included as psoriasis, where psoriatic pain is manifest with rheumatoid arthritis (Chang et al., 2011). The lists do not include ocular pain, discomfort, or other nociceptive conditions originating from the cornea/ocular surface. These are omitted despite the fact that conjunctivitis, a well-known and common condition of the conjunctival tissue, is cited in said patent citations. Conjunctivitis is included in a paragraph dedicated to uses of prostanoid IP antagonists for treating inflammatory pain (U.S. Pat. No. 7,141,584). Thus, it has thereby been defined as somatic pain.

The conjunctiva is one of the anatomically closest tissues to the cornea. Whereas the cornea is clear and with no blood supply, the conjunctiva is a vascularized tissue that can become inflamed and swollen in response to allergic and other inflammatory stimuli. Although the origin of allergic and infectious conjunctivitis is conjunctival tissue, in conjunctivitis there can be sensory symptomology all over the ocular anterior segment, similar to referred pain that may occur with visceral pain. Thus, conjunctivitis could also be arguably considered as akin to not only somatic pain but also visceral pain, according to this criterion.

The symptomatic manifestations of ocular surface and ocular anterior segment diseases are complex and unique to the eye in many respects. This is consistent with sensory receptive elements adapting to and differing according to tissue function. Allergic and infectious diseases usually originate from the conjunctiva. Itch and soreness are prominent symptoms of allergic and infectious conjunctivitis and these neurosensory phenomena likely arise from the conjunctiva. However, studies on conjunctival neurotransmission are very few in number. The technical difficulties of defining sensory receptive fields and isolating nerve fibers emanating from the conjunctiva cannot be surmounted. In short, humans can describe their perceived sensations but nerve conduction cannot be measured and the converse is true in laboratory animals. From these limited studies, it appears that nociceptor populations in the cornea and conjunctiva may mediate quite different sensory modalities. In a study on cold perception, the conjunctiva perceived only a cooling sensation whereas the corresponding corneal sensation included irritation (Acosta et al., 2001). This clearly delineates nociceptor functions in the cornea and conjunctiva.

Certain sensations are, however, common to diseases of the cornea and conjunctiva. These are foreign body sensation and photosensitivity/photophobia. Both are symptoms totally unique to the eye. Foreign body sensation is ubiquitous and may be described as grittiness, sandiness, or a "something in the eye" feeling. Foreign body sensation is discomforting and elicits a desire to rub, wipe, close and/or irrigate the eye. An involuntary response is to increase the blinking (nictation) rate. If severe, foreign body sensation can be intolerably uncomfortable.

The ocular surface neurosensory manifestations may be stratified as follows.
1. Ocular surface discomfort/irritation. This is very common and affects a very significant proportion of the population. Ocular surface discomfort appears to predominantly arise from the cornea. The corneal epithelial layer is densely innervated and is readily activated by physical and chemical insults to the corneal surface and the overlying tear film. Such corneal irritation may arise from drying of the tear film or inadequate tear secretion, immunologically based dry eye disease, and environmental pollutants and contaminants. These insults to the corneal epithelial surface stimulate the nociceptor populations resulting in feelings of dryness, foreign body sensation, irritation and a resultant general discomfort. This degree of nociception may be described as tolerable. Continued dryness or environmental insult may worsen the condition by damaging the corneal epithelium. Persons experiencing ocular surface discomfort typically find some relief by using artificial lubricants. An analgesic drug that would ameliorate the neurosensory activation and associated discomfort would be desirable to achieve more sustained therapy.
2. Ocular pain. This would be best regarded as analogous to the pain associated with inflammatory diseases such as rheumatoid arthritis, degenerative disorders such as osteoarthritis and cancer. A similar or greater level of ocular pain would be caused by alkali or acid burn, penetrating or gross corneal injury, severe microbial infection, or diseases of the ocular anterior segment such as uveitis or severe ocular hypertension. The afflicted individual will typically present in the physician's office or emergency room within 24 hours. A description of intolerable would be applicable to ocular pain.
3. Itch. This is confined to the conjunctiva and is a separate sensation. In all but transient episodes the individual seeks medical treatment. With the exception of treating post-surgical inflammation and pain, the entire spectrum of corneal neurosensory disorders represents an un-met medical need for which there are no commercially available drugs.

A number of neurotransmitters have been proposed as corneal nociceptive mediators. TRPV1 receptors have been widely considered as transducing corneal nociceptive events. Several lines of evidence would support this. TRPV1 receptors are abundant in the cornea (Murata et al., 2006) although not all are associated with polymodal nociceptors (Chen et al., 1997). The TRPV1 receptor stimulant capsaicin activates corneal neurosensory units (Chen et al., 1997) and produces a behavioral response (eye wiping) in laboratory rodents indicative of a nociceptive sensation (Gonzalez et al.; Bates et al., 2010). In humans, capsaicin induces a sharp sensation of pain (Dupuy et al., 1988). Calcium antagonists have also been reported to reduce capsaicin induced ocular pain (Gonzalez et al., 1993). Regardless of these evidences, TRPV1 antagonists such as capsazepine and the widely available $Ca^{2+}$ channel blockers such as diltiazem are not used clinically to treat ocular surface pain and discomfort. TRPV1 inactivation by resininferatoxin (Bates et al., 2010) has not received clinical acceptance for treating corneal neurosensory conditions. Other putative nociceptor mediators such as biogenic amines and neuropeptides have been implicated in corneal pain but this has not translated into clinical utility so far.

Local anesthetics are used to alleviate corneal pain but are used sparingly for rapid but temporary relief. The reason being that local anesthetics prevent any sensation of actual damage or foreign bodies in the exterior of the eye and depress corneal reflexes and blinking. Undetected solid matter on the corneal surface would cause or exacerbate corneal abrasion and heighten corneal nociceptive activity. This would be potentially catastrophic.

The only other therapeutic modality that has found limited utility in treating ocular surface nociception are the Cyclo-oxygenase inhibitors (COXIBs). Cyclo-oxygenase inhibitors (COXIBs) are aspirin-like drugs and are widely as used for treating inflammation, pain, and hyperpyrexia. Their therapeutic actions are due to inhibition of prostanoid biosynthesis. COXIBs are widely used for analgesia and hyperpyrexia and are almost invariably given by mouth. The therapeutic of COXIBs in the eye is much more limited and the route of administration is not oral.

In the eye, COXIBs are used as post-surgical anti-inflammatory agents with analgesic properties and as adjuncts to steroid therapy in treating uveitis. The ophthalmologic practice of COXIB use differs somewhat from that followed in general therapeutics. This is in spite of the fact that the utility of orally administered COXIBs for treating pain is incontrovertible. In ophthalmology, COXIBs are almost invariably applied topically to the ocular surface and are not given by mouth for treating post-surgical inflammation and pain. This is despite the fact that COXIBs are available "over-the-counter" and are eminently affordable. The mechanistic basis of COXIB induced ocular analgesia appears to diverge markedly from that associated with typical systemic therapy. This provides a ready explanation for the topical administration preference in ophthalmology.

The clinical effectiveness of COXIBs used for ophthalmological purposes has been questioned on the basis of their limited efficacy and slow onset (Coppens et al., 2002). From the cyclo-oxygenase inhibition perspective, prostaglandins (PGs) are endogenous constituents of the cornea (Urquhart et al., 2015). Moreover the cornea has no capacity to metabolically inactivate PGs (Cheng-Bennett et al., 1990) and, since the cornea is an avascular tissue, very little capacity to remove PGs from corneal tissue. This would result in very long PG residence times in the cornea. Since the effects of COXIBs depend on prevention PG biosynthesis, the efficacy of COXIBs should not necessarily be apparent until endogenous PGs are replaced by newly synthesized PGs. The effects of COXIBs in the eye are, therefore, more apparent in therapeutic pretreatment and subchronic intervention over days for surgical trauma. Mechanistic studies on COXIB effects on corneal nociception would support the intuitive contention that an alternative analgesic mechanism must exist. In the cornea, COXIBs have been reported to exhibit an alternative analgesic mechanisms of action that is independent of cyclo-oxygenase inhibition and PG biosynthesis. The COXIBs ketorolac, diclofenac, flubiprofen, and nepafenac (Chen et al., 1997; Acosta et al., 2007) all directly attenuated the responsiveness of corneal polymodal nociceptor fibers. Further, diclofenac and flurbiprofen directly inhibit ASIC induced neurosensory transmission (Voilley et al., 2001). This is of significance since ASIC nociceptors are involved in pain (Wemmie et al., 2013) and ocular surface discomfort (Callejo et al., 2015). Inhibition of ocular surface nociception may represent effects that are made manifest after the tissue concentrations sufficient to inhibit cyclo-oxygenase enzymes have been far exceeded. Nevertheless, the doses used in ophthalmologic nociception studies reflect those used clinically and, therefore, likely represent the in-life clinical situation. Direct inhibition of TRP and ASIC nociceptors by COXIBs seems a more plausible mechanistic explanation than inhibition of prostanoid biosynthesis.

Considering pre-formed and resident PGs as an impediment to successful treatment of corneal nociception by inhibition of cyclo-oxygenase inhibition using COXIB drugs, this therapeutic mechanism of action merits serious consideration. The identity of PG receptors possibly involved in corneal nociception has not been systematically elucidated. COXIBs have an advantage in that they suppress PG biosynthesis and thereby produce global inhibition of PG effects in the cornea. However, since PGs exist preformed in the cornea and COXIB effects depend on blocking de novo PG biosynthesis, prevention of PG receptor stimulation may represent a better therapeutic strategy. Restated in a different way, a prostanoid receptor antagonist may block the activity of preformed prostaglandins in the cornea by directly blocking their interaction with their target receptors. Prostanoid receptor pharmacology is discussed below.

The prostanoids are oxygenated fatty acids with potent and diverse biological activities. They are biosynthesized from arachidonic acid by cyclo-oxygenase enzymes, the intermediate endoperoxides then being converted to a range of different prostanoids by specific prostaglandin synthase enzymes. The major biologically active prostanoids are prostaglandins $D_2$, $E_2$, and $F_2$, prostacyclin ($PGI_2$), and thromboxane $A_2$. These prostanoids exert their biological effects by interacting with a series of receptor proteins, which preferentially interact with one of the major prostanoids, as follows. Thus, prostaglandin $D_2$ preferentially interacts with $DP_1$ and $DP_2$ receptors, prostaglandin $E_2$ with $EP_{1-4}$ receptors, prostaglandin $F_2a$ with FP receptors, prostacyclin with IP receptors and thromboxane $A_2$ with TP receptors (Woodward et al., 2011).

All of the major prostanoids have been implicated in pain and inflammation (Kawakarni et al., 2001; Ueno et al., 2001; Kunori et al., 2009; Woodward et al., 2011; Gatta et al., 2012; Kanda et al., 2013). This may explain why inhibitors of the cyclo-oxygenase enzymes 1 and 2 are extensively used as analgesics and receptor selective antagonists are not. Although potent and selective antagonists for each of the individual prostanoid receptors have been developed over many years, none have found favor as clinically useful analgesics. Indeed, the prostanoid EP receptor was initially viewed as the most likely nociceptor involved in pain (Woodward et al., 2011) and selective $EP_1$ antagonist drugs were developed and studied clinically. These have not found clinical utility as analgesics.

Consideration of prostacyclin and its target receptor (IP) receptor as a mediator in pain could be viewed as counterintuitive because of its exceptionally short biological half-life (Cho and Allen, 1978). IP antagonists have been studied in three of the four categories of "pain", namely somatic, visceral, peripheral and neuropathic. Experimental evidence exists for a role in somatic inflammatory pain, visceral pain, neuropathy induced nociception, and hyperalgesia. No evident inclusion of peripheral nociception is apparent. In models of inflammatory pain, gene deletion and IP receptor antagonists have been reported as effective analgesics (Bley et al., 2006; Woodward et al., 2011). In IP receptor knockout mice, the pain associated with the writhing response to acetic acid was dramatically reduced (Murata et al., 1997). This signifies a role in visceral pain (Ohishi et al., 1999; Huang et al., 2010). In addition to analgesic activity in acute models, IP receptor antagonism also reduces the pain and inflammation in models of hyperalgesia and chronic arthritis (Pulichino et al., 2006). Prostacyclin has also been implicated in the central processing of neurotransmission (Doi et al., 2002; Nakae et al., 2005; Schuh et al., 2014). In one study, however, although the IP receptor agonist iloprost indicated a functional role for prostacyclin in exciting dorsal root ganglia, virtually all prostanoid receptors sensitized rat dorsal root ganglia (Nakae et al., 2005). Nevertheless, such nociception produced by IP agonists in rodent cellular and living animal studies would be complimentary to the IP antagonist studies. A detailed anatomical analysis of prostacyclin in pain transmission is difficult because all of the reports to date do not distinguish between central or local transmission of nociceptive responses. All of these studies were performed in mice or rats, which several authors acknowledged in the titles of their articles. In a clinical study in human rheumatoid arthritis subjects, the IP receptor agonist iloprost was found to improve markers of inflammation and reduce joint pain swelling, tenderness and pain (Gao et al., 2002). This constitutes an absolute contradiction of results obtained in rat and mouse studies and renders rodent models of pain unreliable. The limited predictive value of mice and rats compared to primates is a documented concern with respect to clinical translation (Vierboom et al., 2008). For the reasons described above and the unique nociceptive qualities of the ocular surface described below, non-human primates were chosen as the species of choice for the purpose of translational reliability. Moreover, a known clinical condition was replicated in the monkeys, namely mild corneal abrasion.

The proposed involvement of prostanoid IP receptors in mediating and processing inflammatory pain responses has been its origins in rodent models of inflammation. These models result in inflammatory pain that exhibits certain characteristics akin to those that are frequently encountered in rheumatoid arthritis and other inflammatory diseases. For example, pressure on the affected area or limb exacerbates and/or creates pain. Applying pressure by standing on the affected load-bearing limb(s) is painful and devices have been invented to automatically monitor pressure applied by small animal footpads to a touch sensitive plate; less pressure being applied by the swollen and/or painful limb. Movement of affected limbs exacerbates or creates local pain, this can often be severe to the point where fear of movement becomes a very distressing factor in persons with inflammatory and neuropathic pain.

Nociceptive events on the ocular surface produce an entirely different repertoire of behaviors and sensations to those encountered in inflammatory pain from, for example, rheumatoid conditions. Squeezing and/or pressing the eye actually relieves ocular pain. An increased nictation rate also results. Rubbing the eyes to remove the perceived foreign body also occurs, especially in animals where the foreign body sensation cannot be construed as a "phantom" syndrome. The cornea is an avascular tissue, therefore tissue swelling and leukocyte infiltration do not contribute to nociceptive responses as would be the case in solid vascularized tissues and joints.

Prostaglandins participate in the inflammation associated with cataract surgery and pain associated with corneal refractive surgery. Cyclo-oxygenase inhibitors (COXIBs) such as ketorolac are used as surgical adjuncts and for photoradialkeratotomy (PRK), whereas selective prostanoid receptor antagonists have not been employed for these therapeutic indications. Cyclo-oxygenase inhibitors (COXIBs) have not found extensive use for ocular surface disorders, beyond being used as post-surgical adjuncts. One factor that may influence the use of COXIBs in ocular surface disorders is the long duration of prostanoid residence in the cornea; the cornea has little capacity to enzymatically deactivate prostaglandins (Cheng-Bennett et al., 1990) and the cornea is avascular. Therefore, once biosynthesized in the cornea, prostaglandins have a very long residence time. It follows that the utility of cyclo-oxygenase inhibitors may be compromised in post-treatment dosing regimens, where prostaglandins are already resident at elevated levels in the cornea: these drugs can prevent prostanoid biosynthesis but cannot affect prostanoids already formed and present. In contrast, a receptor antagonist can directly compete with the prostaglandins already resident in the cornea for their receptors and thereby reverse their effects. This is an important therapeutic consideration. The patient usually presents at the physician's office or emergency room with a pre-existing condition that is affecting ocular wellbeing. It is, therefore, of considerable therapeutic significance that a prostanoid IP receptor antagonist can actually reverse the nociception in a primate model of ongoing discomfort/irritation.

SUMMARY OF INVENTION

The present invention describes compounds and methods of treating ocular surface nociception by using a prostanoid IP receptor antagonists. One such prostanoid IP receptor antagonist is 4,5-dihydro-N-[4-[[4-(1-methylethoxy)phenyl]methyl]phenyl]-1H-imadazol-2-amine (RO-1138452, CAY 10441):

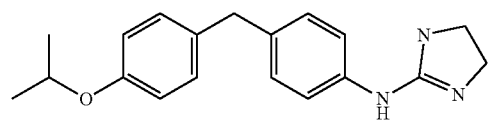 [SMILES: CC(C)Oc1ccc(Cc2ccc(NC3=NCCN3)cc2)cc1]

and its physiologically acceptable salts.

This is an IP antagonist that also recognizes platelet activating factor (PAF) receptors (Woodward et al., 2011). 4,5-dihydro-N-[4-[[4-(1-methylethoxy)phenyl]methyl]phenyl]-1H-imadazol-2-amine and its congeners are described in U.S. Pat. Nos. 6,184,242; 6,472,536; 6,596,876; 6,693,200; and 7,141,584, which are hereby incorporated by reference in their entireties.

Other IP antagonists of the present invention include:

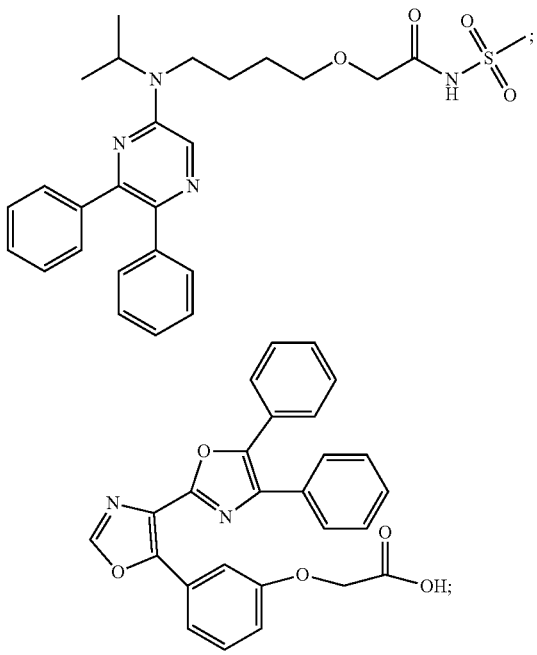

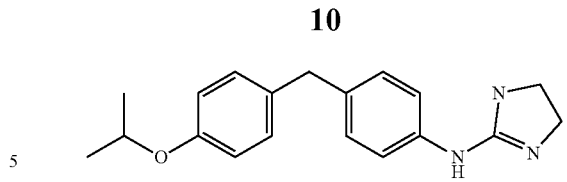

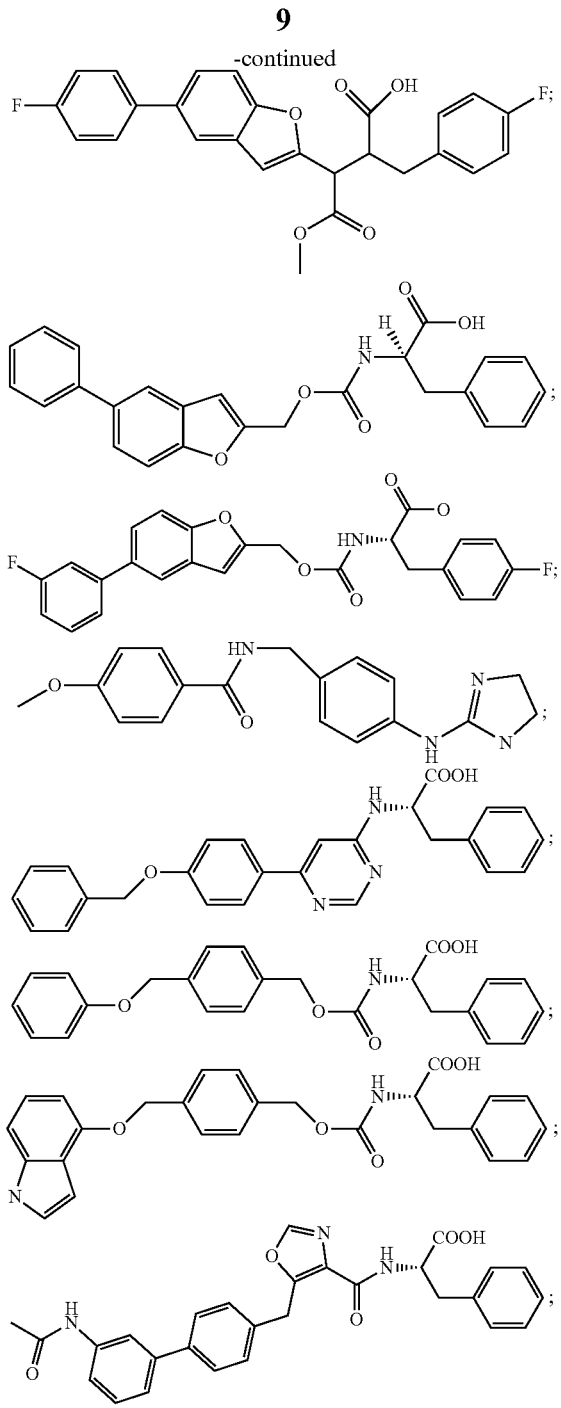

and their physiologically acceptable salts.

The invention pertains to the symptomology of ocular surface discomfort produced by environmentally or disease induced dry eye, ocular surface injury, ulceration, infection, allergy, environmental pollution, infection, and surgery. This symptomology, for example, variably includes a feeling of dryness and/or grittiness, foreign body sensation, burning and stinging and photosensitivity. Moreover, the use of an IP receptor antagonist allows reversal of a pre-existing ocular disorder and its associated ocular symptomology.

Some embodiments of the Invention include:
1) A method of treating ocular nociception in a patient comprising administering to the eyes of the patient the following compound:

2) The method of embodiment 1 including pharmaceutically acceptable salts.
3) The method of embodiments 1 or 2 wherein the compound is administered in an ophthalmologically acceptable composition.
4) The method of embodiment 3 wherein the ophthalmologically acceptable composition is one selected from the group consisting of a solution, an emulsion, a dispersion, a suspension, an ointment and a gel.
5) The method of embodiment 3 wherein the ophthalmologically acceptable composition is an ocular implant.
6) The method of embodiment 3 wherein the ophthalmologically acceptable composition is a solution and is selected from the formulations and compositions of Tables 1 and 2.
7) The method of embodiments 1-6 wherein the method results in a significant reduction of ocular nociception.
8) The method of embodiment 1 wherein the ocular nociception is associated with the ocular surface.
9) The method of embodiments 1 and 8 wherein the compound interacts with prostanoid IP receptors.
10) The method of embodiments 1-9 wherein the ocular nociception is produced by one selected from the group consisting of environmentally or disease induced dry eye, ocular surface injury, ulceration, infection, allergy, environmental pollution and surgery.
11) The method of embodiments 1, 8 and 9 wherein the compound interacts with TRPV1 receptors.
12) A method of relieving ocular pain and/or ocular discomfort comprising administering to the eyes of the patient a compound selected from the group consisting of:

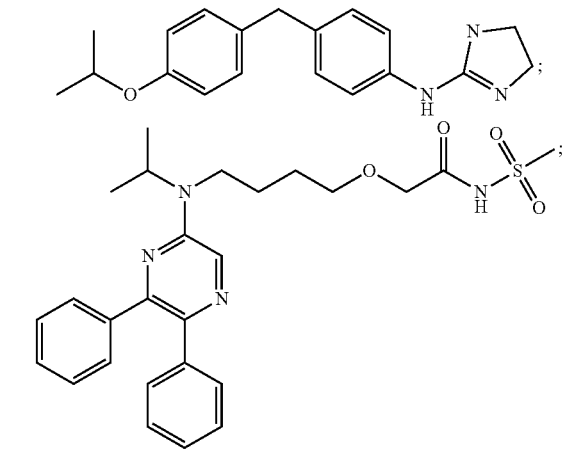

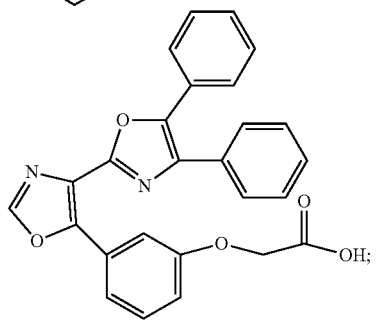

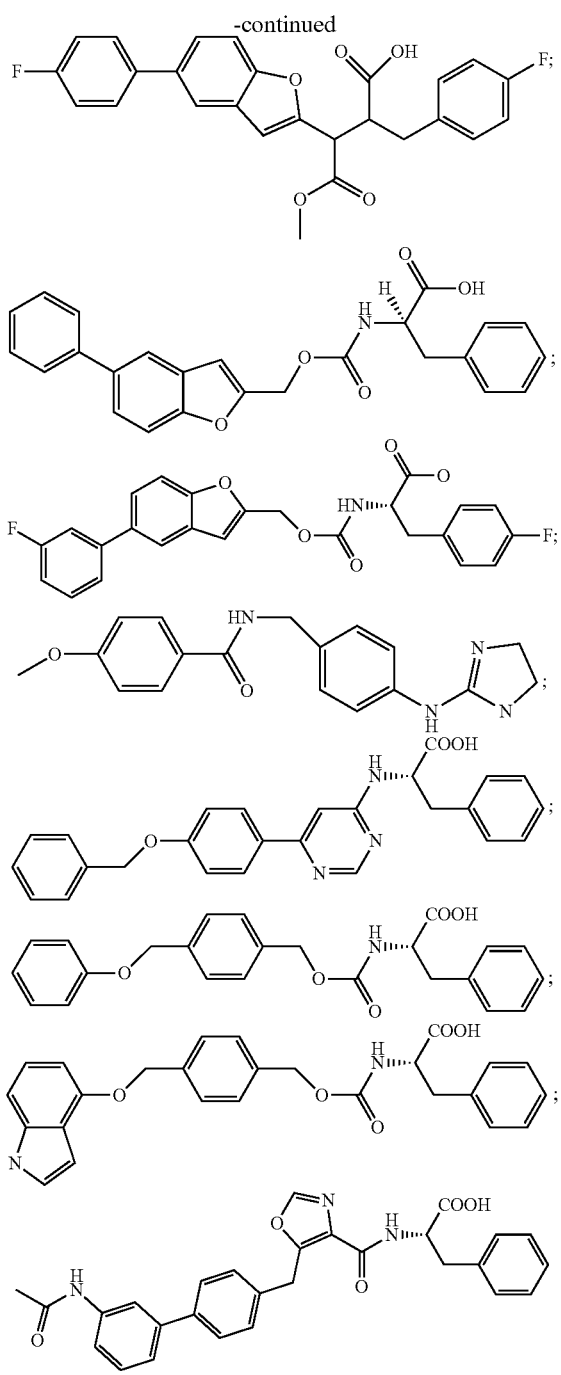

and their pharmaceutically acceptable salts.

13) The method of embodiment 12 wherein the compound is administered in an ophthalmologically acceptable composition.

14) The method of embodiment 13 wherein the ophthalmologically acceptable composition is one selected from the group consisting of a solution, an emulsion, a dispersion, a suspension, an ointment and a gel.

15) The method of embodiment 13 wherein the ophthalmologically acceptable composition is an ocular implant.

16) The method of embodiment 13 wherein the ophthalmologically acceptable composition is a solution and is selected from the formulations and compositions of Tables 1 and 2.

17) The method of embodiments 11-16 wherein the method results in a significant reduction of ocular pain and/or ocular discomfort.

18) The method of embodiment 12 wherein the ocular nociception is associated with the ocular surface.

19) The method of embodiments 1 and 12 wherein the compound interacts with prostanoid IP receptors.

20) The method of embodiments 12-19 wherein the ocular nociception is produced by one selected from the group consisting of environmentally or disease induced dry eye, ocular surface injury, ulceration, infection, allergy, environmental pollution, infection, and surgery.

21) The method of embodiments 12, 18 and 19 wherein the compound interacts with TRPV1 receptors.

22) A method of treating dry eye comprising administering a composition comprising:

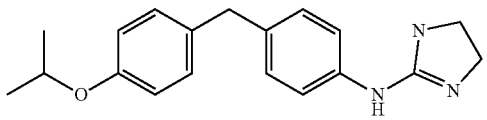 [SMILES: CC(C)Oc1ccc(Cc2ccc(NC3=NCCN3)cc2)cc1]

and its pharmaceutically acceptable salts.

23) The method of embodiment 22 wherein the composition treats both dry eye and pain associated with dry eye.

24) The method of embodiments 22 and 23 wherein the dry eye is selected from the group consisting of autoimmune positive dry eye, aqueous tear deficient dry eye, and evaporative dry eye.

25) The method of embodiments 1 and 12 wherein the ocular pain or ocular discomfort is caused by one selected from the group consisting of post-surgical pain, dry eye, alkali burn, acid burn, penetrating corneal injury, gross corneal injury, severe microbial infection, or diseases of the ocular anterior segment such as uveitis or severe ocular hypertension.

26) The method of embodiment 25 wherein the pain is one selected from the group consisting of somatic, visceral, peripheral and neuropathic pain.

27) A method of reversing the effects of prostaglandins resident in the cornea by administering a composition comprising a compound selected from the group consisting of:

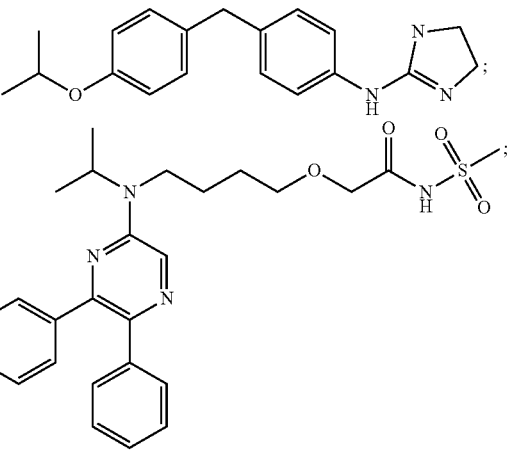

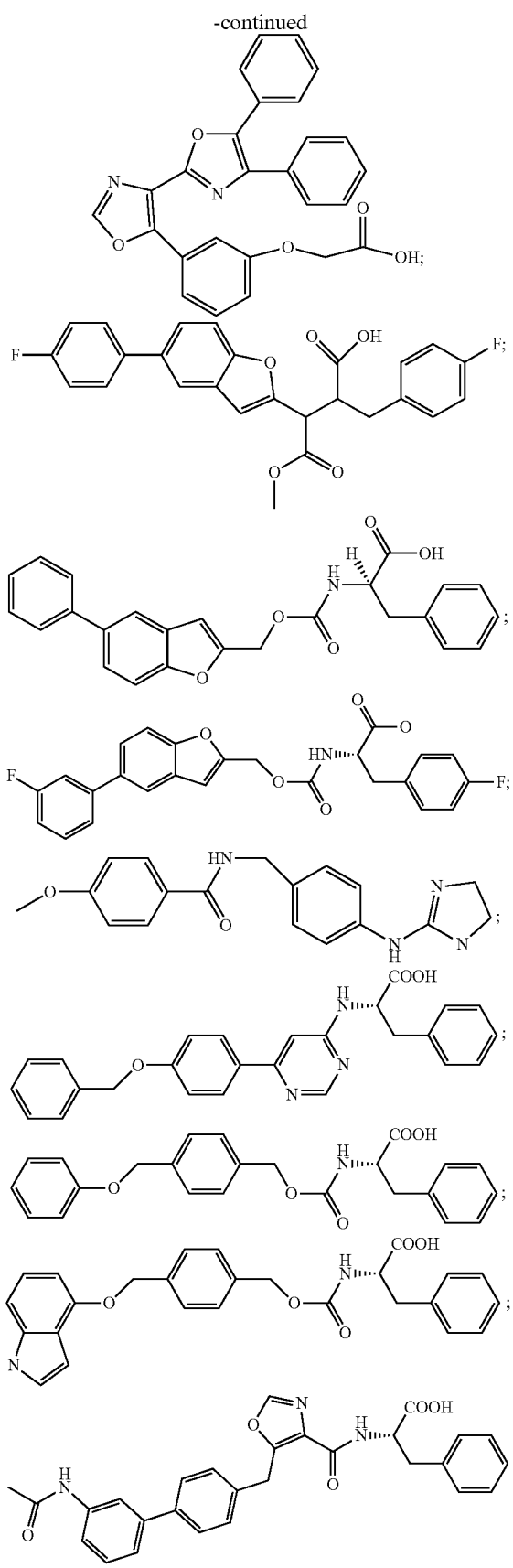

and their pharmaceutically acceptable salts.

28) The method of embodiment 27 wherein reversing the effects of prostaglandins resident in the cornea reduces ocular pain and discomfort for the patient.

29) A method of treating ocular pain or ocular discomfort after eye surgery with at least one of the compounds of embodiment 27 wherein the eye surgery is selected from the group consisting of refractive surgery, laser eye surgery, cataract surgery, glaucoma surgery, canaloplasty, refractive surgery, corneal surgery, vitroretinal surgery, eye muscle surgery, oculoplastic surgery, eyelid surgery, orbital surgery, and surgery involving the lacrimal apparatus.

30) The method of embodiment 29 wherein the eye surgery is cataract surgery selected from the group consisting of phacoemulsification, extracapsular cataract surgery and intracapsular cataract surgery.

31) The method of embodiment 29 wherein the eye surgery is glaucoma surgery and is selected from the group consisting of laser surgery and conventional surgery.

32) The method of embodiment 29 wherein the eye surgery is refractive surgery and is selected from the group consisting of keratomilleusis, automated lamellar keratoplasty, laser assisted in-situ keratomileusis, laser assisted sub-epithelial keratomileusis, photorefractive keratectomy, laser thermal keratoplasty, conductive keratoplasty, limbal relaxing incisions, astigmatic keratotomy, transverse keratotomy, radial keratotomy, mini asymmetric radial keratotomy, hexagonal keratotomy, epikeratophakia, intracorneal rings, implantable contact lenses, presbyopia reversal, anterior ciliary sclerotomy, and scleral reinforcement surgery for the mitigation of degenerative myopia.

33) The method of embodiment 29 wherein the eye surgery is corneal surgery and is selected from the group consisting of corneal transplant surgery, penetrating keratoplasty, keratoprosthesis, phototherapeutic keratectomy, pterygium excision, corneal tattooing and osteo-odonto-keratoprosthesis.

34) The method of embodiment 29 wherein the eye surgery is vitroretinal surgery selected from the group consisting of vitrectomy such as an anterior vitrectomy, pars plana vitrectomy, trans pars plana vitrectomy, pan retinal photocoagulation, retinal detachment repair such as ignipuncture, laser photocoagulation, pneumatic retinopexy, retinal cryopexy, macular hole repair, partial lamellar sclerouvectomy, partial lamellar sclerocyclochoroidectomy, partial lamellar sclerochoroidectomy, posterior sclerotomy, radial optic neurotomy, and macular translocation surgery.

35) The method of embodiment 29 wherein the eye surgery is eyelid surgery selected from the group consisting of blepharoplasty, ptosis repair for droopy eyelid, ectropion repair, entropion repair, canthal resection, canthectomy, cantholysis, canthopexy, canthoplasty, canthorrhaphy, canthotomy, lateral canthotomy, epicanthoplasty and tarsorrhaphy.

36) The method of embodiment 29 wherein the eye surgery is orbital surgery selected from the group consisting of orbital reconstruction, ocular prosthetics and orbital decompression for Grave's Disease.

37) The method of embodiment 29 wherein the eye surgery is eye surgery on the lacrimal apparatus.

38) A method of relieving ocular nociception comprising administering a prostanoid IP receptor antagonist.

39) The method of embodiments 1 or 12 wherein the compound is also a platelet activating factor.

40) A method of preparing an ophthalmic solution, suspension, or emulsion using one of the compounds from embodiment 12 wherein the pH is 5.5-8.5 and the concentration range of the composition 0.003%-5%.

41) A method for treating ocular pain or ocular discomfort by combining an IP receptor antagonist, such as one from embodiment 12, with an ocular surface lubricating agent such as polyethylene glycol, propylene glycol, polyvinyl alcohol, castor oil and glycerol.

42) A method where a prostanoid IP antagonist, such as that selected from embodiment 12, wherein the IP antagonist is combined with cyclosporine or a cyclosporine analog thereof for the treatment of dry eye disease.

43) A method where a prostanoid IP antagonist, such as that selected from embodiment 12, wherein the IP antagonist is combined with a glucocorticoid for the treatment of dry eye disease, inflammatory, allergic ocular diseases, and other ocular diseases where glucocorticoids would be considered beneficial.

44) A method where a prostanoid IP receptor antagonist, such as that selected from embodiment 12, wherein the IP antagonist is combined with a non-steroidal anti-inflammatory for the treatment of ocular inflammatory disease, allergic ocular diseases, dry eye diseases and as a post-surgical adjunct.

45) A method where a prostanoid IP receptor antagonist, such as that selected from embodiment 12, wherein the IP antagonist is combined with an antibiotic to treat infectious diseases of the ocular surface.

46) A method where a prostanoid IP receptor antagonist, such as that selected from embodiment 12, wherein the IP antagonist is combined with an antihistamine for treating allergic conjunctivitis.

47) The method of embodiments 1 and 12 wherein the composition is administered in conjunction with an anti-allergy drug is selected from the group consisting of alcaftadine, cromolyn, dexamethasone, difluprednate, fluorometholone, loteprednol, rimexolone, azelastine, epinastine, emedastine difumarate, olopatadine, cromolyn ophthalmic, lodoxamide, nedocromil, bromfenac, diclofenac, flurbiprofen, ketorolac, nepafenac, loradatine, hydroxyzine, diphenhydramine, chlorpheniramine, azelastine hydrochloride brompheniramine, cyproheptadine, terfenadine, clemastine, levocabastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, pemirolast, chiorcyclizine, thonzylamine and/or mixtures of at least two thereof.

48) The method of embodiments 1 and 12 wherein the composition is administered in conjunction with an antineoplastic agent is selected from the group consisting of cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, flutamide, adriamycin, cyclophosphamide, actinomycin, bleomycin, duanorubicin, doxorubicin, epirubicin, mitomycin, methotrexate, fluorouracil, carboplatin, carmustine (BCNU), and methyl-CCNU and/or mixtures of at least two thereof.

49) The method of embodiments 1 and 12 wherein the composition is administered in conjunction with an antibiotic and is selected from the group consisting of ampicillin, amoxicillin, cyclacillin, ampicillin, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, gentamicin, tobramycin, besifloxacin, ciprofloxacin, gatifloxacin, levofloxacin, moxifloxacin, ofloxacin, azithromycin, erythromycin, bacitracin, bacitracin/polymyxin, natamycin, neomycin/polymyxin B/bacitracin, neomycin/polymyxin B/gramicidin, polymyxin B/trimethoprim, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, and trimethoprim and/or mixtures of at least two thereof.

50) The method of embodiments 1 and 12 wherein the composition is administered in conjunction with a β-adrenergic receptor blocker and is selected from the group consisting of acebutolol, atenolol, labetalol, metoprolol, propranolol, timolol maleate and/or mixtures of at least two thereof.

51) The method of embodiments 1 and 12 wherein the composition is administered in conjunction with an anti-inflammatory agent, including steroids, NSAIDs (non-Steroidal Anti-Inflammatory Drugs), COX inhibitors, or prostanoid receptor inhibitors blocking single or multiple receptors. Corticoands, such as cortisone, prednisolone, flurometholone, dexamethasone, medrysone, loteprednol fluazacort, hydrocortisone, prednisone, betamethasone, methylprednisolone, riamcinolone hexacatonide, paramethasone acetate, diflorasone, fluocinonide, fluocinolone, and triamcinolone; non-steroidal anti-inflammatory agents, such as aspirin, diclofenac, rofecoxib, ibuprofen, indomethacin; PG antagonists and/or mixtures of at least two thereof.

52) The method of embodiments 1 and 12 wherein the composition is administered in conjunction with an immunomodulating agent is selected from the group consisting of cyclosporine, azathioprine, methotrexate, and tacrolimus and/or mixtures of at least two thereof.

53) The method of embodiments 1 and 12 wherein the composition is administered in conjunction with an antiviral agent selected from the group consisting of interferon gamma, zidovudine, amantadine hydrochloride, ribavirin, acyclovir, valciclovir, dideoxycytidine, phosphonoformic acid, ganciclovir and/or mixtures of at least two thereof.

54) The method of embodiments 1 and 12 wherein the composition is administered in conjunction with a drug selected from the group consisting of phentolamine, testosterone, dexamethasone, bimatoprost, latanoprost, travoprost, tafluprost, pilocarpine, brimonidine tartrate and/or mixtures of at least two thereof.

55) The compounds of embodiments 1 and 12 wherein the compound may be administered systemically.

56) 4,5-dihydro-N-[4-[[4-(1-methylethoxy)phenyl]methyl]phenyl]-1H-imadazol-2-amine for the manufacture of a medicament for the treatment of ocular pain or discomfort which may be applied from one selected from the group consisting of every one, two, three, four, five, six, seven, eight, nine, or ten times a day.

57) The use of 4,5-dihydro-N-[4-[[4-(1-methylethoxy)phenyl]methyl]phenyl]-1H-imadazol-2-amine for the manufacture of a medicament for treating of ocular pain or ocular discomfort.

58) The methods of embodiments 1 and 12 wherein the composition is administered topically to the front of the eye.

59) The methods of embodiments 1 and 12 wherein the composition is administered periorbitally.

60) The compounds of embodiments 1 and 12 wherein the compounds are delivered in a composition to the front of the eye or periorbitally wherein the composition is comprised of glycerine, castor oil, polysorbate 80, carbomer, purified water and sodium hydroxide.

61) The compounds of embodiment 60 wherein the carbomer is carbomer 1342.

62) The compounds of embodiments 1 and 12 wherein the compounds are delivered in a composition to the front of the eye or periorbitally wherein the composition is comprised of carbomer 1342, castor oil, glycerine, mannitol, polysorbate 80, sodium hydroxide to adjust pH, and purified water.

63) The compounds of embodiment 59 wherein the compounds are administered in one selected from the group consisting of an oil, cream or gel.

64) The compounds of embodiment 63 wherein the oil, cream or gel has at least penetration enhancer selected from the group consisting of oleyl alcohol, Transcutol® and polyethylene glycol.

BRIEF DESCRIPTION OF THE DRAWINGS

FIG. 1 shows the results of corneal abrasion induced eye pain/discomfort on Cynomologous monkeys from day 1 to day 5 and the data is % eye blinking, with the level of nictation rate just before drug treatment normalized and set to 100%.

FIG. 2 shows FIG. 1 from Days 4 to Day 5, which are the days showing drug treatment effects.

DETAILED DESCRIPTION OF THE INVENTION

The terms "about", "approximate" and "approximately" are used herein to modify a numerical value and indicate a defined range around that value. If "X" were the value, "about X" or "approximately equal to X" would generally indicate a value from 0.90× to 1.0X. Any reference to "about X" minimally indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%." About may also refer to a number close to the cited number that would result in a bioequivalent therapeutic effect by a regulatory agency such as the FDA or the EMEA.

The terms "active", "active agent", "active pharmaceutical ingredient", "API" and "drug" refer to the active ingredient of a composition. An API is typically a chemical substance or mixture of chemical substances. Such substances are intended to furnish pharmacological activity or other direct effect in the diagnosis, cure, mitigation, treatment or prevention of disease of the eye.

"Chemoreceptors"—a sensory cell or organ responsive to chemical stimuli.

The term "daily" means every day and may refer to once a day or multiple times a day such as BID or TID dosing.

The terms "effective amount," "therapeutically effective amount" or "pharmaceutically effective amount" refer to an amount of an active agent effective to treat ocular pain or ocular discomfort or other ophthalmic diseases, including a range of effects, from a detectable amount of improvement to substantial relief/improvement of symptoms or a cure of the disease or condition. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in an ophthalmic disease. For example, for the given aspect (e.g., length of incidence), a therapeutically effective amount will show an increase or decrease of at least 5%, 10%, 15%, 20%, 25%, 40%, 50%, 60%, 75%, 80%, 90%, or 100%. Therapeutic efficacy can also be expressed as "-fold" increase or decrease. For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

"Emulsion" means, but is not limited to, an oil-in-water emulsion, a water-in-oil emulsion, a micro emulsion referring to particle sizes of $10^{-9}$.

"Formulation" and "composition," are intended to be equivalent and refer to a composition of matter suitable for pharmaceutical use (i.e., producing a therapeutic effect as well as possessing acceptable pharmacokinetic and toxicological properties).

"Mechanoreceptors" a sense organ or cell that responds to mechanical stimuli such as touch or sound.

"Polymodal nociceptors": a receptor that responds to several different forms of sensory stimulation (as heat, touch, and chemicals)

"Ocular Discomfort" is an annoying ocular surface sensation that is tolerable

"Ocular Pain" is an unpleasant intolerable sensation located to the globe and eye socket "Ocular Surface" is the cornea and sclera and its associated bulbar conjunctiva "Ocular Surface Injury" refers to damage to the corneal surface caused by physical injury or disease.

"Ophthalmic acceptable composition" is a composition that can be administered to the eye.

"Pharmaceutically acceptable" is used as equivalent to physiologically acceptable. In certain embodiments, a pharmaceutically acceptable composition or preparation will include agents for buffering and preservation in storage, and can include buffers and carriers for appropriate delivery, depending on the route of administration.

"Post surgical pain" is pain resulting from ocular surgery

The terms "subject," "patient," "individual," are not intended to be limiting and can be generally interchanged. That is, an individual described as a "patient" does not necessarily have a given disease, but may be merely seeking medical advice. The term "subject" as used herein includes all members of the animal kingdom prone to suffering from the indicated disorder. In some aspects, the subject is a mammal, and in some aspects, the subject is a human.

"Significant reduction in ocular pain" a statistically significant reduction according to Student's non-paired t test.

"Thermoreceptors" are sensory receptors, usually a nerve ending in the skin, that is stimulated by heat or cold.

"Treating" or "treatment" as used herein includes any approach for obtaining beneficial or desired results in a subject's condition, including clinical results. Beneficial or desired clinical results can include, but are not limited to, alleviation or amelioration of one or more symptoms or conditions, diminishment of the extent of a disease or treatment of ocular pain or ocular discomfort, stabilizing (i.e., not worsening) the state of disease, delay or slowing of disease progression, amelioration, diminishment of the reoccurrence of disease. Treatment may prevent the disease from occurring; relieve the disease's symptoms, fully or partially remove the disease's underlying cause, shorten a disease's duration, or do a combination of the above.

"Treating" and "treatment" as used herein may also include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for duration sufficient to treat the patient.

As used herein, "topical", "topical application," "topical administration," and "topically administering" are used interchangeably herein and include the administration to the front of the eye of a subject. Topical application or administering may result in the delivery of an active agent to the eye.

"Topical formulation" and "topical pharmaceutical composition" are used interchangeably herein and include a formulation that is suitable for topical application to the eye. A topical formulation may, for example, be used to confer a therapeutic benefit to its user.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids.

Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

The compositions can be administered prior to, concurrently with, and/or after the development of ocular discomfort or ocular pain or any other eye disease or condition. The compositions may be administered for a period of time necessary to achieve the desired results, which may be several days to several months or continuously. The compositions can be administered once or several times (2, 3, 4, or more times) a day depending on the desired effect. In certain embodiments, the compositions can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 days or until the ocular pain or discomfort disappears. In another embodiment, the compositions can be administered one or more times every 1, 2, 3 or 4 weeks. The administration can be on an occasional basis such as monthly or bi-monthly basis or when needed by the patient. Further, the compositions can be administered for 1, 2, 3, 6, 9 or 12 months or continuously. In certain embodiments, the compositions can be administered on an ongoing basis to maintain a desired result. The compositions can be administered once a day, twice a day, three times a day and up to four times a day.

The compounds and compositions described herein may be administered at least in the minimum dose necessary to achieve the desired therapeutic effect. Generally, such doses may be in the range of 50-100 μl/day or per dosing or about 0.005 mg/day to about 1 mg/day. In another example embodiment, the compound or active agents may be present in a composition or formulation in a range of about 50-1000 μl/week or 0.005-10 mg/week. However, the actual amount of the compound to be administered in any given case will be determined by a physician taking into account the relevant circumstances, such as the age and weight of a patient, patient's general physical condition, severity of the ocular pain or other eye condition or disease. In some instances, dosing is evaluated on a case-by-case basis.

The pH of the disclosed compositions can be about 3 to about 8.0, or about 6.5 to about 7.5. In certain embodiments, the pH of the formulation is about 7.0 to about 7.4 or about 7.1 to about 7.3.

Additionally, compositions may be designed to delay release of the compound over a given period of time such as in an ocular implant, or to carefully control the amount of compound released at a given time during the course of treatment.

Table 1 lists possible aqueous vehicle formulations in the form of solutions of 4,5-dihydro-N-[4-[[4-(1-methylethoxy)phenyl]methyl]phenyl]-1H-imadazol-2-amine but it is intended that any drug referenced in the specification or any prostanoid IP receptor antagonist may be included ("Active Agent").

TABLE 1

| Ingredient | Aqueous Vehicle Formulations | | | | | | | | | | |
|---|---|---|---|---|---|---|---|---|---|---|---|
| % w/v | 1 | 2 | 3 | 4 | 5 | 6 | 7 | 8 | 9 | 10 | 11 |
| Active agent | 0.1 | 0.2 | 0.3 | 0.5 | 0.1 | 0.15 | 0.02 | 0.03 | 0.035 | 0.05 | 0.04 |
| NaCl | 0.1 | 0.2 | 0.15 | 0.2 | 0.1 | 0.15 | — | 0.1 | 0.2 | 0.3 | 0.2 |
| EDTA | 0.01 | 0.02 | 0.015 | 0.01 | 0.02 | 0.015 | 0.03 | — | 0.01 | — | 0.02 |
| Mannitol | 1.0 | — | 2.0 | 2.5 | — | 1.0 | 2.0 | — | 5.0 | 2.0 | 3.0 |
| Glycerin | 10.0 | — | 4.0 | 5.0 | 10 | 5 | 10 | — | 5 | 10 | — |
| BAK | 0.15 | 0.2 | 0.1 | 0.2 | — | 0.1 | 0.2 | 0.1 | 0.2 | — | 0.2 |
| Castor Oil | 0.25 | — | 0.2 | 0.5 | — | 1.0 | 0.5 | 0.1 | 1.0 | — | 1.0 |
| Polysorbate 40 | — | 0.1 | — | — | — | 0.3 | — | — | — | — | — |
| Oleyl Alcohol | 0.1 | — | — | 0.5 | — | 0.2 | — | — | 0.1 | 0.1 | — |
| Transcutol ® | 0.05 | 0.2 | — | — | 0.1 | — | — | 0.05 | — | 0.05 | 0.2 |
| Ethanol | 1% | — | 1.5% | 2.0% | 1.0% | — | — | 0.5% | 2.0% | 1.0% | — |
| Boric Acid | — | 1.5% | 1.6% | — | 1.9% | 1.7% | — | — | 1.8% | — | 1.5% |
| Propylene Glycol | — | — | 0.2 | — | 0.1 | 0.01 | 0.1 | 0.1 | — | — | — |

Table II lists possible compositions of creams and gels for ocular administration. Table II lists possible vehicle compositions in the form of creams or gels of 4,5-dihydro-N-[4-[[4-(1-methylethoxy)phenyl]methyl]phenyl]-1H-imadazol-2-amine but it is intended that any drug referenced in the specification of any prostanoid IP receptor antagonist may be included ("Active Agent"):

TABLE 2

| Ingredient | Function | Composition (% w/w) | | | | | | | | |
|---|---|---|---|---|---|---|---|---|---|---|
| | | 1 | 2 | 3 | 4 | 5 | 6 | 7 | 8 | 9 |
| Active Agent | Active | 0.1 | 0.2 | 0.3 | 0.4 | 0.5 | 0.01 | 0.02 | 0.03 | 0.04 |
| PEG 400 | Solubilizer | 20 | 25 | — | 15 | 20 | 25 | 20 | — | — |
| Diethylene glycol monoethyl ether | Solubilizer | 25 | 20 | 15 | 20 | 25 | — | 25 | 25 | 25 |
| Lactic Acid | Solubilizer | 5 | 10 | — | 10 | 5 | 10 | 10 | — | 5 |
| Dimethyl Isosorbide | Solubilizer | — | — | — | — | 15 | — | — | — | — |
| Isopropyl Myristate | Solubilizer | — | — | 10 | — | — | 5 | — | 10 | — |
| Carboxymethyl Cellulose | Thickener | 5 | — | 20 | 10 | 15 | 10 | — | 5 | 25 |
| Hydroxyethyl Cellulose | Thickener | 20 | 25 | 5 | 10 | 15 | 10 | 20 | 5 | — |
| Glycerin | Humectant | 10 | 10 | — | — | — | 10 | 10 | 2 | — |
| EDTA Disodium | Antioxidant | 0.01 | 0.01 | 0.01 | 0.01 | 0.01 | 0.01 | 0.01 | 0.01 | — |
| Citric Acid | Antioxidant | 0.03 | 0.03 | 0.03 | 0.03 | 0.03 | 0.03 | 0.03 | 0.03 | — |
| Propylene Glycol | Penetration Enhancer | 10 | — | — | 20 | 10 | 20 | — | 20 | 15 |
| Oleyl Alcohol | Penetration Enhancer | 5 | 3 | 5 | — | 5 | 10 | 15 | — | — |
| Benzyl Alcohol | Preservative | 1.0 | 2.0 | 1.5 | — | 1.0 | 2.0 | 1.5 | 1.0 | — |
| Purified Water | Solubilizer | Q.S. | Q.S. | Q.S. | Q.S. | Q.S. | Q.S. | Q.S. | Q.S. | Q.S. |

No preservative is required with unit dose compositions in Tables 1 and 2.

No preservative is required with unit dose compositions in Tables 1 and 2.

Preservatives of the vehicles of Tables 1 and 2 and in compositions throughout the application may be substituted with the following preservatives expressed in % w/v or % w/w:
  Na-borate/Boric Acid 1.5%-1.9%;
  Polyhexamthethylene biguanide (PHMB) from 0.0001%-0.02%;
  Parabens (parahydroxy benzoic acid derivatives;
  Phenyl mercuric nitrate;
  benzalkonium chloride 0.004%-0.02%
  benzelthonium chloride up to 0.010%
  chlorhexidine 0.005% to 0.01%
  chlorbutanol up to 0.5%
  methyl paraben 0.03-0.1%
  phenylethyl alcohol up to 0.5%
  phenylmercuric acetate 0.002-0.004%
  phenylmercuric nitrate 0.002-0.004%
  propyl paraben up to 0.01%
  thimerosol up to 0.01%

The active agent, which may be any drug referenced in the specification, may be present in the following concentrations from a percent w/v or w/w of about 0.01 to about 0.15, from about 0.02 to about 0.15, from about 0.03 to about 0.15, from about 0.04 to about 0.15, from about 0.05 to about 0.15, from about 0.06 to about 0.15, from about 0.07 to about 0.15, from about 0.08 to about 0.15, from about 0.09 to about 0.15, from about 0.1 to about 0.15, from about 0.11 to about 0.15, from about 0.115 to about 0.15, from about 0.120 to about 0.15, and from about 0.125 to about 0.15, from about 0.125 to about 0.145, from about 0.125 to about 0.14, from about 0.02 to about 0.08, from about 0.03 to about 0.08, from about 0.04 to about 0.08, from about 0.05 to about 0.08, from about 0.06 to about 0.08, from about 0.07 to about 0.08, from about 0.02 to about 0.07, from about 0.03 to about 0.07, from about 0.04 to about 0.07, from about 0.05 to about 0.07, from about 0.06 to about 0.07, from about 0.02 to about 0.06, from about 0.03 to about 0.06, from about 0.04 to about 0.06, from about 0.05 to about 0.06, from about 0.02 to about 0.05, from about 0.03 to about 0.05, from about 0.04 to about 0.05, from about 0.02 to about 0.04, from about 0.03 to about 0.04, or from about 0.02 to about 0.03%. In other embodiments, the active agent may be present at about 0.01, 0.02, 0.03, 0.04, 0.05, 0.06, 0.07, 0.08, 0.09, or 0.1, 0.11, 0.12, 0.121, 0.122, 0.125, 0.13, 0.135, 0.140, 0.145, 0.150, 0.155, 0.160, 0.165, 0.170, 0.175, 0.180, 0.185, 0.190, 0.195, 0.2, 0.25, 0.30, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 and 10.0 (% w/v) or (% w/w).

Example I

A prostanoid IP receptor antagonist (4,5-dihydro-N-[4-[[4-(1-methylethoxy)phenyl]methyl]phenyl]-1H-imadazol-2-amine RO-1138452, CAY 10441), at a dose of 0.3% w/v in an aqueous 1% polysorbate 80 in Tris-HCL (a standard ocular vehicle used in testing of ophthalmic drugs), was administered topically to the ocular surface of twelve Cynomolgus monkeys. Cynomologus monkeys are the closest animal model for humans. A model that replicates an actual clinically encountered ocular condition, namely corneal abrasion, was employed.

As an animal model indicative of both ocular discomfort and pain, mild corneal scarification and measurement of the resultant increased blinking (nictation) rate was employed. The species chosen was the Cynomologous monkey and there are reasons for this selection. The Cynomologus monkeys have similar vision to humans, its eye is structurally similar to humans, and it is the closest species phylogenetically to man Although superior to common laboratory animal species for ocular nociceptive studies, the monkey has the disadvantage of being incapable of communicating perceived ocular sensations and it is necessary to rely on behaviors indicative of pain, irritation, and discomfort. Increased rate of blinking (nictation) is recognized as a reliable end-point indicative of discomfort and pain and was, therefore, used in the studies described herein. There is a linear correlation between ocular surface sensory-evoked stimulation and blink rate in humans (Wu et al., 2014). Increased blinking frequency is associated with a diverse variety of conditions that elicit ocular discomfort and pain such as air borne noxious contaminants (Lang et al., 2008), acidic solutions (Collejo et al, 2015), dry eye conditions and wearing contact lenses (Wu et al., 2014). Thus, increased blinking rate is a universal indicator of ocular surface nociception resulting in discomfort and pain.

The drug formulation was administered post-scarification of the cornea, and at identical time points on two subsequent days. Ocular discomfort was monitored as the nictation (blinking) rate. Blinking is an established human behavioral response to corneal discomfort and irritation (Lang et al., 2008; Wu et al., 2014; Callejo et al., 2015). In setting up the monkey model of ocular surface discomfort, it was noted that increased blink rate remained part of a greater response to increased scarification width or topical capsaicin, where eye closure/squinting and scleral redness presented as additional symptoms. This degree of nociception was part of preliminary "sighting" experiments and was unintended and involved few animals. The detailed and final experimental protocol is provided as follows, with activities on each day detailed.

A total of eight naïve Cynomolgus monkeys were used. They were divided into two groups of four. The nictation rate (blinking rate) was measured to provide quantification of discomfort. The daily study protocol was as follows. The monkeys were not permanently harmed and were treated according to the highest standard of ethics.

Day 1:
Time 0 hr (e.g. 8:00 am): Measure nictation rate and assess clarity of cornea, lacrimation, and conjunctival congestion.
Time 10 hr (e.g. 6:00 pm): Measure nictation rate and assess clarity of cornea, lacrimation, and conjunctival congestion.

Day 2:
Time 0 hr (e.g. 8:00 am): Measure nictation rate and assess clarity of cornea, lacrimation, and conjunctival congestion.
Time 10 hr (e.g. 6:00 pm): Measure nictation rate and assess clarity of cornea, lacrimation, and conjunctival congestion.

Day 3:
Time 0 hr (e.g. 8:00 am): Measure nictation rate and assess clarity of cornea, lacrimation, and conjunctival congestion. Then scarify the left cornea of each of the 8 monkeys.
Time 1 hr (e.g. 9:00 am): Measure nictation rate and assess clarity of cornea, lacrimation, and conjunctival congestion.
Time 2 hr (e.g. 10:00 am): Measure nictation rate and assess clarity of cornea, lacrimation, and conjunctival congestion.
Time 4 hr (e.g. 12:00 am): Measure nictation rate and assess clarity of cornea, lacrimation, and conjunctival congestion.
Time 10 hr (e.g. 6:00 pm): Measure nictation rate and assess clarity of cornea, lacrimation, and conjunctival congestion.

Day 4:
Time 0 hr (e.g. 8:00 am): Measure nictation rate and assess clarity of cornea, lacrimation, and conjunctival congestion. Then apply the drug 4,5-dihydro-N-[4-[[4-(1-methylethoxy)phenyl]methyl]phenyl]-1H-imadazol-2-amine) (0.3% w/v) to the left cornea of each of the 4 monkeys. Then apply vehicle to the left cornea of each of the other 4 animals.
Time 1 hr (e.g. 9:00 am): Measure nictation rate and assess clarity of cornea, lacrimation, and conjunctival congestion.
Time 2 hr (e.g. 10:00 am): Measure nictation rate and assess clarity of cornea, lacrimation, and conjunctival congestion.
Time 4 hr (e.g. 12:00 am): Measure nictation rate and assess clarity of cornea, lacrimation, and conjunctival congestion.
Time 10 hr (e.g. 6:00 pm): Measure nictation rate and assess clarity of cornea, lacrimation, and conjunctival congestion.

Day 5:

Time 0 hr (e.g. 8:00 am): Measure nictation rate and assess clarity of cornea, lacrimation, and conjunctival congestion. Then apply the drug (4,5-dihydro-N-[4-[[4-(1-methylethoxy)phenyl]methyl]phenyl]-1H-imadazol-2-amine, 0.3% w/v) to the left cornea of each of the 4 monkeys. Then apply the vehicle to the left cornea of each of the other 4 monkeys.

Time 1 hr (e.g. 9:00 am): Measure nictation rate and assess clarity of cornea, lacrimation, and conjunctival congestion.

Time 2 hr (e.g. 10:00 am): Measure nictation rate and assess clarity of cornea, lacrimation, and conjunctival congestion.

Time 4 hr (e.g. 12:00 am): Measure nictation rate and assess clarity of cornea, lacrimation, and conjunctival congestion.

Time 10 hr (e.g. 6:00 pm): Measure nictation rate and assess clarity of cornea, lacrimation, and conjunctival congestion.

FIG. 1 shows the effect of topically applied IP antagonist drug (4,5-dihydro-N-[4-[[4-(1-methylethoxy)phenyl]methyl]phenyl]-1H-imadazol-2-amine), at a 0.3% w/v concentration, on the discomfort associated with mild corneal abrasion. Monkeys that received vehicle are represented by the black line, monkeys that received drug are represented by the gray line. Drug and vehicle were given at 8:00 am of each experimental day depicted. Values are mean % blink rate following drug or vehicle treatment compared to day 4, 8:00 am baseline (100%): n=4 per group, P<0.01 comparing vehicle and drug treated groups.

The effect of topically applied IP antagonist drug (4,5-dihydro-N-[4-[[4-(1-methylethoxy)phenyl]methyl]phenyl]-1H-imadazol-2-amine), given once daily at a 0.3% w/v concentration, on the discomfort associated with mild corneal abrasion is shown in FIG. 1. Animals that received vehicle showed a clinically significant rate of increase in nictation rate over the two day period, the nictation rate was statistically significantly lower in the drug treated eyes. Nictation rate (blinking) demonstrates the extent of ocular pain, which is a standard method in showing relief of ocular pain in animals.

During Days 1-3, there was no difference in terms of handling/treatment in control vs. treated group in Day 1-3. During Day 1 and Day 2, the pre-surgical blinking baseline was measured in these two days.

Day 3 was the day of surgery, then wait 24 hours to get the blinking rate stabilize before treatment. Comparing to the baseline in Day 1-2 (mean=83%), there was an increase in blinking rate after the surgery (Data not shown in slide #1) and the post-surgery blinking baseline (=100%). The actual study started on Day 4.

Day 4 at 8 am nictation/Blinking rate=100%, i.e. the blinking rate at 24 hour after scarification of the cornea is set as 100%, all blinking rates are normalized to this control point. The ocular scarification was controlled at a degree that it should not cause the animals severe pain and visible inflammation, so the discomfort from the lesion did not last too long. This is why two days after the surgery (Day 5-16:00), the difference in blinking rate is minimal in the control vs. treated group.

The results show that the IP antagonist drug (4,5-dihydro-N-[4-[[4-(1-methylethoxy)phenyl]methyl]phenyl]-1H-imadazol-2-amine) significantly reduced ocular surface nociception induced by scarification (P≤0.01 non-paired t-test) and therefore controls ocular pain.

Example II

A 55-year old Caucasian male was suffering from extreme ocular discomfort which was associated with pain. The 55 year old Caucasian male adds a 0.3% w/v solution of 4,5-dihydro-N-[4-[[4-(1-methylethoxy)phenyl]methyl]phenyl]-1H-imadazol-2-amine and experiences an immediate reduction of ocular pain. The 55-year old Caucasian male continues to add the 0.3% w/v solution twice a day and then all pain is reduced and eventually disappears.

Example III

A 36-year old Hispanic female suffers a grade 2 chemical eye burn from an acidic substance. Despite being administered prednisolone acetate 1% every two hours, severe ocular pain persists. The physician will administer Formula 3 from Table I, three times a day. Within twelve hours of administration, the patient feels a significant reduction in ocular pain, which leads to less nictation and rubbing of her eyes and faster healing. After 7-21 days, the patient experiences corneal/conjunctival epithelium and keratocytes proliferate. Collagen synthesis begins.

Example IV

A 41-year old African American construction worker is struck by debris while working, some of which implants into his cornea and he suffers from a corneal foreign body. Unfortunately, the patient does not receive prompt medical attention. The foreign body entered into the anterior chamber of the eye, resulting in slight ocular necrosis, resulting in long-term pain. The patient will be administered Formula 5 from Table 1 up to 4 times a day for treatment of chronic pain until the patient's eye is healed.

Example V

A 78-year old Caucasian female, living in a very dry and arid climate, develops autoimmune positive dry eye needing prompt medical attention. The doctor prescribes Composition 3 from Table 2 which will be given 4 times daily for treatment of autoimmune dry eye. Within a week the autoimmune dry eye symptoms disappear.

Example VI

A 60-year old Hispanic female suffers from aqueous tear deficient dry eye associated occasionally with moderate to severe sharp ocular pain. The doctor prescribes Formulation 7 of Table 1 twice a day and the dry eye and ocular pain improves immediately and the symptoms disappear completely after 7 days.

Example VII

A 35-year old Caucasian female lives in an arid region and frequently suffers from evaporative dry eye associated with occasional sharp pains that use of artificial tears does not prevent. After being prescribed once a day use of Formulation 6 from Table I, the 35 year old Caucasian patient's eyes no longer experience sharp pains and the dry eye symptoms improve.

Example VIII

A 62 year old Asian male has laser in-situ keratomileusis ("LASIK") surgery to correct near sightedness and after the surgery suffers from severe ocular pain and dry eye, which are common side effects with L-ZIK surgery. The patient's ophthalmologist prescribes Composition 5 of Table 2 TID until the patient's symptoms improve and then administered BID.

Example IX

An 81 year old Caucasian female patient undergoes an operation to remove cataracts. After the surgery the patient experiences intolerable ocular pain. The patient's ophthalmologist prescribes Formulation 8 of Table I TID until the patient's ocular pain symptoms improve.

Example X

A 73 year old Caucasian male undergoes corneal transplant surgery. After the surgery, the patient experiences severe ocular pain. The patient's ophthalmologist prescribes Formulation 9 BID until the patient's ocular pain symptoms improve.

What is claimed:

1. A method of treating dry eye disease in a patient comprising administering to the patient a therapeutically effective amount of 4,5-dihydro-N-[4-[[4-(1-methylethoxy)phenyl]methyl]phenyl]-1H-imadazol-2-amine, or a pharmaceutically acceptable salt thereof.

2. The method of claim 1, wherein the 4,5-dihydro-N-[4-[[4-(1-methylethoxy)phenyl]methyl]phenyl]-1H-imadazol-2-amine is administered in a topical ophthalmic formulation to one or both eyes of the patient.

3. The method of claim 2, wherein the topical ophthalmic formulation is administered once a day.

4. The method of claim 2, wherein the topical ophthalmic formulation is administered twice a day, three times a day or up to four times a day.

5. The method of claim 2, wherein the topical ophthalmic formulation is one selected from the group consisting of a solution, an emulsion, a dispersion, a suspension, an ointment and a gel.

6. The method of claim 2, wherein the 4,5-dihydro-N-[4-[[4-(1-methylethoxy)phenyl]methyl]phenyl]-1H-imadazol-2-amine is present in the topical ophthalmic formulation in an amount of about 0.003% (w/v) to about 10% (w/v).

7. The method of claim 2, wherein the 4,5-dihydro-N-[4-[[4-(1-methylethoxy)phenyl]methyl]phenyl]-1H-imadazol-2-amine is present in the topical ophthalmic formulation in an amount of about 0.01% (w/v) to about 0.15% (w/v).

8. The method of claim 2, wherein the topical ophthalmic formulation is administered topically to the front of the eye.

9. The method of claim 2, wherein the topical ophthalmic formulation is administered periorbitally.

10. The method of claim 1, wherein the dry eye disease is selected from the group consisting of aqueous tear deficient dry eye disease and evaporative dry eye disease.

11. The method of claim 1, further comprising administering cyclosporine or a cyclosporine analog.

12. A method of treating dry eye disease and pain associated with dry eye disease in a patient comprising administering to at least one eye of the patient a therapeutically effective amount of 4,5-dihydro-N-[4-[[4-(1-methylethoxy)phenyl]methyl]phenyl]-1H-imadazol-2-amine, or a pharmaceutically acceptable salt thereof, in a topical ophthalmic formulation.

13. The method of claim 12, wherein the topical ophthalmic formulation is administered topically to the front of the eye or periorbital skin.

14. The method of claim 12, wherein the topical ophthalmic formulation is one selected from the group consisting of a solution, an emulsion, a dispersion, a suspension, an ointment and a gel.

15. The method of claim 12, wherein the 4,5-dihydro-N-[4-[[4-(1-methylethoxy)phenyl]methyl]phenyl]-1H-imadazol-2-amine is present in the topical ophthalmic formulation in an amount of about 0.003% (w/v) to about 10% (w/v).

16. The method of claim 12, wherein the dry eye disease is selected from the group consisting of aqueous tear deficient dry eye disease and evaporative dry eye disease.

* * * * *